(12) United States Patent
Tannous et al.

(10) Patent No.: US 7,128,894 B1
(45) Date of Patent: Oct. 31, 2006

(54) CONTRAST ENHANCING SOLUTION FOR USE IN CONFOCAL MICROSCOPY

(75) Inventors: Zeina Tannous, Boston, MA (US); Abel Torres, Loma Linda, CA (US); Salvador González, Newton, MA (US)

(73) Assignee: The United States of America as represented by the United States Department of Energy, Washington, DC (US)

( * ) Notice: Subject to any disclaimer, the term of this patent is extended or adjusted under 35 U.S.C. 154(b) by 405 days.

(21) Appl. No.: 10/607,630

(22) Filed: Jun. 27, 2003
(Under 37 CFR 1.47)

Related U.S. Application Data

(60) Provisional application No. 60/392,515, filed on Jun. 27, 2002.

(51) Int. Cl.
*A61K 49/00* (2006.01)
(52) U.S. Cl. .................................... 424/9.1
(58) Field of Classification Search ............. None
See application file for complete search history.

(56) References Cited

U.S. PATENT DOCUMENTS

| | | | |
|---|---|---|---|
| 4,395,398 A * | 7/1983 | Yamamoto | 424/642 |
| 5,494,793 A | 2/1996 | Schindele et al. | |
| 6,159,445 A * | 12/2000 | Klaveness et al. | 424/9.6 |
| 6,187,289 B1 * | 2/2001 | Richards-Kortum et al. | 424/9.8 |
| 6,402,037 B1 | 6/2002 | Prasad et al. | |
| 6,540,981 B1 | 4/2003 | Klaveness et al. | |
| 6,652,840 B1 * | 11/2003 | Prevendar | 424/49 |

OTHER PUBLICATIONS

Rajadhyaksha et al., J. Invest. Dermatol. 1999, 113: 293-303.*

* cited by examiner

*Primary Examiner*—Larry R. Helms
*Assistant Examiner*—Hong Sang
(74) *Attorney, Agent, or Firm*—Daly, Crowley, Mofford & Durkee, LLP

(57) ABSTRACT

A method of optically detecting a tumor during surgery. The method includes imaging at least one test point defined on the tumor using a first optical imaging system to provide a first tumor image. The method further includes excising a first predetermined layer of the tumor for forming an in-vivo defect area. A predetermined contrast enhancing solution is disposed on the in-vivo defect area, which is adapted to interact with at least one cell anomaly, such as basal cell carcinoma, located on the in-vivo defect area for optically enhancing the cell anomaly. Thereafter the defect area can be optically imaged to provide a clear and bright representation of the cell anomaly to aid a surgeon while surgically removing the cell anomaly.

11 Claims, 6 Drawing Sheets

CONTRAST ENHANCING SOLUTION FOR USE IN CONFOCAL MICROSCOPY

CROSS REFERENCE TO RELATED APPLICATIONS

This application claims benefit of U.S. Provisional Patent Application No. 60/392,515, filed Jun. 27, 2002, entitled, Aluminum Chloride As Contrast Enhancer for In-Vivo Optical Detection of Tumors During Surgery, which application is hereby incorporated by reference in its entirety.

STATEMENTS REGARDING FEDERALLY SPONSORED RESEARCH

This invention was made with Government support under Grant No. DE-FG02-91ER61228 awarded by the U.S. Department of Energy. The Government may have certain rights to this invention.

FIELD OF THE INVENTION

The present invention relates generally to the optical detection of tumors during surgery and, more particularly, to enhancing the optical detection of tumors.

BACKGROUND OF THE INVENTION

As is known in the art, confocal microscopy is an imaging technique that can optically image biological objects using confocal microscopes. Confocal microscopes vary in configuration and location of components, but in order to simplify the description, confocal microscopes can be assumed to all function in a similar manner. In a typical confocal microscope, light is directed through a set of holes in a disk, e.g., a Nipkow disk. As the disk spins, the holes that are illuminated produce a scanning pattern similar to that produced by the electron gun of a television tube. Optically, the holes act as pinholes and permit only parallel rays of light to pass. The light exiting the pinholes passes through an objective lens and onto the tissue. Light reflected from the tissue passes back through the objective lens and the pinholes and may be collected by a video camera. The image captured by the video camera can be digitized, computer enhanced, and viewed on a video monitor, stored in a digital or analog form, and/or printed on paper.

The depth to which the confocal microscope can optically penetrate to permit in-vivo observation in real-time is limited by the light penetration into the tissue and the reflective properties of the structures being observed. One skilled in confocal microscopy will recognize that the structures should reflect some light to be visible. Only the light reflected from the biologic structures at the selected plane is allowed to pass into the image plane and to contribute to image formation. Because both the light and the microscope objective lens are focused at the same specific focal plane, objects and structures above and below the plane do not interfere with the formed image.

Attempts to enhance the reflective characteristics of skin tumors and/or lesions typically require that the tumors and/or lesions be excised using Mohs micrographic surgery and then treated for increasing the reflective characteristics thereof. More particularly, Mohs micrographic surgery (MMS) is a surgical procedure based on microscopically controlled excision of cutaneous neoplasms. It offers the highest cure rates among other therapeutic modalities while maximally preserving surrounding normal skin. This therapeutic modality is the treatment of choice for neoplasms in high-risk locations where functional and cosmetic reconstruction is limited, and for histologic tumor subtypes with aggressive biologic behavior. MMS involves excision of the clinically apparent tumor and/or lesion, processing and staining of horizontal frozen sections of the tumor and/or lesion using reagents, such as hematoxylin and eosin or toluidine blue, stepwise microscopic analysis, meticulous mapping of tumor and/or lesion extensions, and re-excision of residual portions of the tumor and/or lesion until tumor-free margins are obtained. Preparation of frozen stained sections of the tumor and/or lesion can require approximately 20–60 minutes per stage. Therefore, Mohs surgery can be a tedious, time-consuming and costly surgical procedure requiring correlating the positive histology with actual skin margins. Although MMS is a tissue-sparing surgical technique, it can still result in the sacrifice of some noninvolved or otherwise healthy tissue.

It would, therefore, be desirable to overcome the aforesaid and other disadvantages.

SUMMARY OF THE INVENTION

The present invention provides a method of enhancing optical characteristics of at least one cell anomaly associated with a tumor. With this arrangement, a surgeon or medical technician can efficiently identify and demarcate the at least one cell anomaly associated with the tumor for subsequent removal. While the invention is primarily shown and described in conjunction with enhancing the contrast of a tumor and/or lesion, it is understood that the invention is applicable to other cell anomalies in general in which contrast enhancement is desirable.

In one aspect of the invention, a method of enhancing optical characteristics of at least one cell anomaly associated with a tumor includes applying a predetermined contrasting solution to an in-vivo defect area associated with the tumor for optically enhancing the at least one cell anomaly associated with the tumor. The method further includes imaging at least a portion of the in-vivo defect area associated with the tumor using a first optical imaging system, such as a confocal microscope, to provide an in-vivo enhanced tumor image. The in-vivo enhanced tumor image includes the at least one cell anomaly having enhanced attributes, which aids a surgeon or medical tecnician in identifying and demarcating the at least one cell anomaly associated with the tumor. In the exemplary embodiment, applying the predetermined contrasting solution to the in-vivo defect area includes applying an AlCl solution having a predetermined concentration of Al and a predetermined concentration of Cl.

BRIEF DESCRIPTION OF THE DRAWING

The foregoing and other objects of this invention, the various features thereof, as well as the invention itself, can be more fully understood from the following description, when read together with the accompanying drawings in which.

DETAILED DESCRIPTION OF THE INVENTION

The present invention provides a system and method for enhancing the optical detection of tumors during surgery. The system and method assists a surgeon in optically locating the margins or boundaries of tumors and/or lesions, so that the surgeon can surgically remove the tumors and/or lesions while at the same time minimizing the unnecessary removal of healthy tissue.

Figure 1:
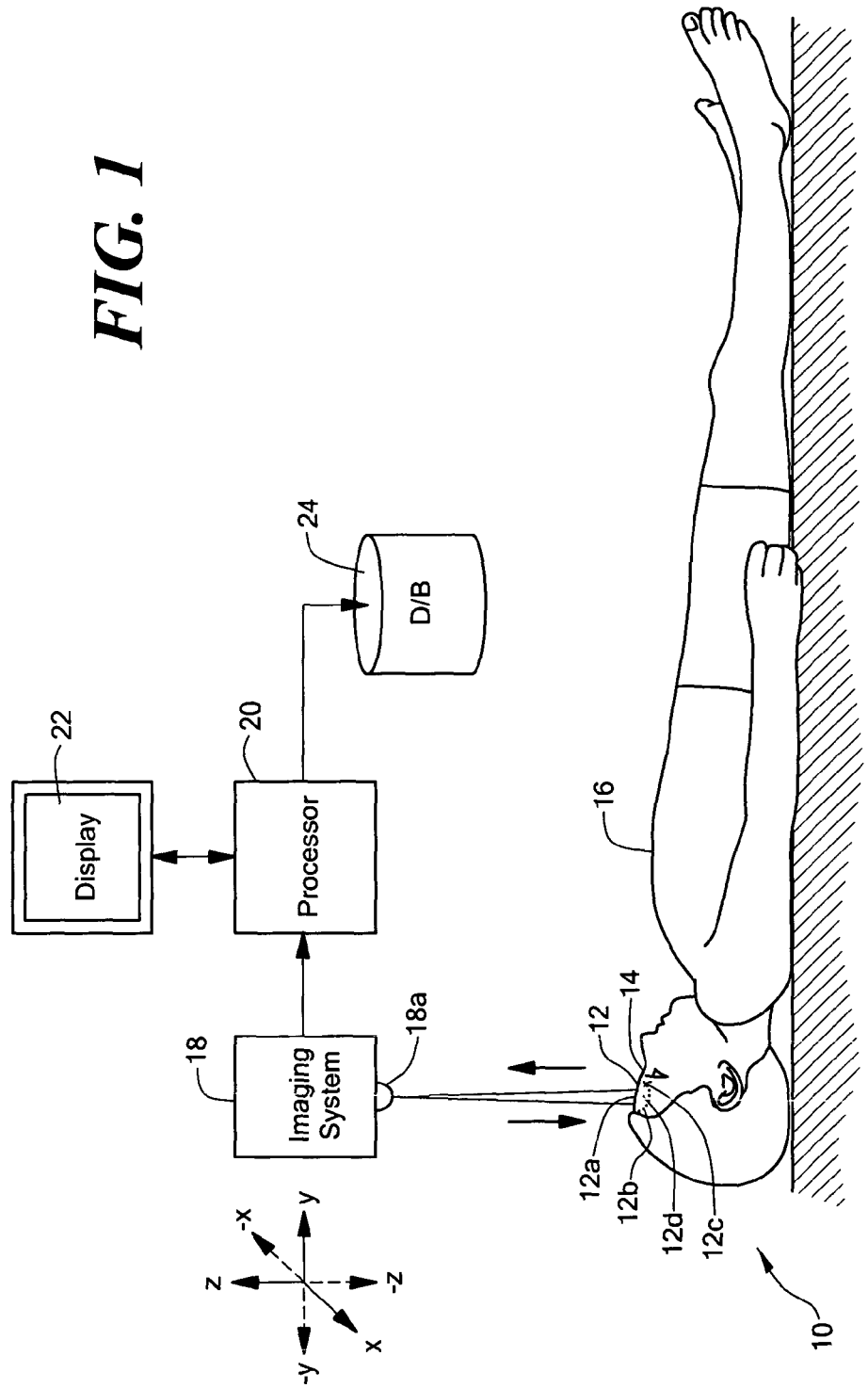
FIG. 1 is a system for the optical detection of tumors during surgery in accordance with the present invention.

Referring now to FIG. 1, shown is an exemplary embodiment of a system 10 for enhancing the optical detection of a tumor and/or lesion 12 located on a patient 16 during surgery. The system 10 includes an imaging system 18 coupled to a processor 20. The processor 20 is coupled to a display 22 and to a database 24. In an embodiment, the tumor and/or lesion 12 (hereinafter referred to as "tumor 12") is located on a forehead region 14 of the patient 16.

As part of preliminary preparation of the patient 16 for surgery, a surgeon or medical technician can mark a first test point 12a on a central region of the tumor 12 using a surgical marking pen, which serves as an imaging test point. Further, the surgeon or medical technician can mark a margin or boundary 12b about the circumference of the tumor 12, which provides a surgical guide to the surgeon during subsequent excision of the tumor 12. The surgeon or medical technician can also mark a second point 12c that traverses the boundary 12b of the tumor 12 for providing a registration point of the tumor 12 after excision thereof from the patient 16. The remaining wound formed as a resultant of excision of the tumor 12 defines a Mohs defect area 12d, as will be described further below.

In the exemplary embodiment, the imaging system 18 is defined as a confocal microscope, which is adapted for imaging human skin. One specific example of a confocal microscope suitable for imaging human skin includes a Vivascope 1000, which can be provided by Lucid, Inc., of Henrietta, N.Y. Although not specifically described herein, it should be understood that a number of other types of imaging systems can be employed as the imaging system 18 including, but limited to, scanning electron microscopes (SEMs), high power cameras and/or white-light tanden confocal SEMs.

In the exemplary embodiment, the processor 20 can include a conventional computer server, such as an "NT-Server," which can be provided by Microsoft of Richmond, Wash., a "Unix Solaris Server," which can be provided by Sun Micro Systems of Palo Alto, Calif. or any one of a number of personal computers, as are known. The processor 20 can be programmed to enhance attributes of a plurality of images of tumors, which are collected by the imaging system 18, and to display the enhanced images of the tumors on the display 22 for evaluation by physicians and/or medical technicians.

In the exemplary embodiment, the image display 22 can include a color cathode-ray tube (CRT), liquid crystal display (LCD), plasma display, or the like, which is adapted to display the plurality of images of tumors. The plurality of images of tumors, which will be described in detail below in connection with FIGS. 3A, 3B, 4A and 4B, may be stored in the database 24 and can be retrieved for further processing, comparisons and/or evaluations at a later time.

Figure 2:
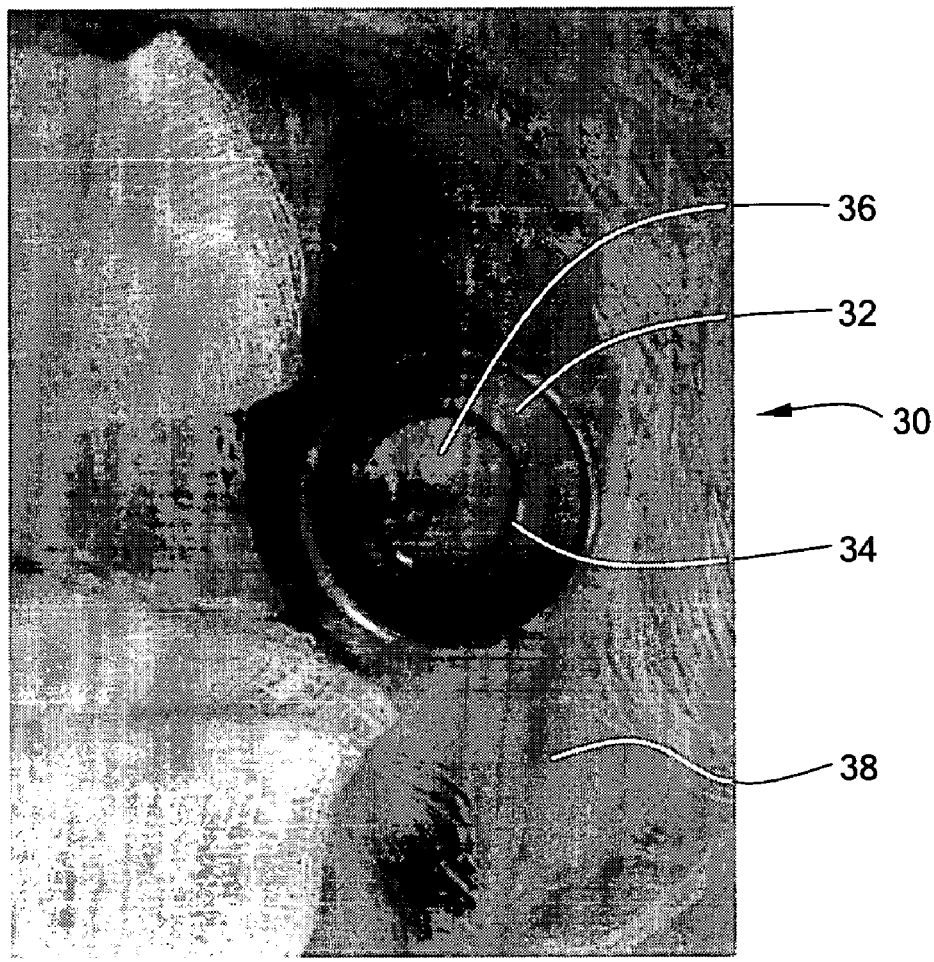
FIG. 2 is a tissue ring used in conjunction with the system of FIG. 1.

Referring to FIG. 2, shown is an exemplary embodiment of a tissue ring 30, which is used in connection with the imaging system 18 shown and described above with respect to FIG. 1, as will be described in further detail below. The tissue ring 30 includes a relatively rigid and sturdy ring 32 that is adapted to removeably accept an objective lens 18a (FIG. 1) of the imaging system 18 (FIG. 1). The tissue ring 30 further includes an aperture 34, which includes a barrier lens 36. The barrier lens 36 may serve to focus a light beam, which is provided by the imaging system 18, onto the skin surface of the patient under inspection. The barrier lens 36 may also serve to maintain a sterile barrier or separation space between the objective lens 18a of the imaging system 18 and the skin surface 38 of the patient 16 under inspection.

Figure 3A:
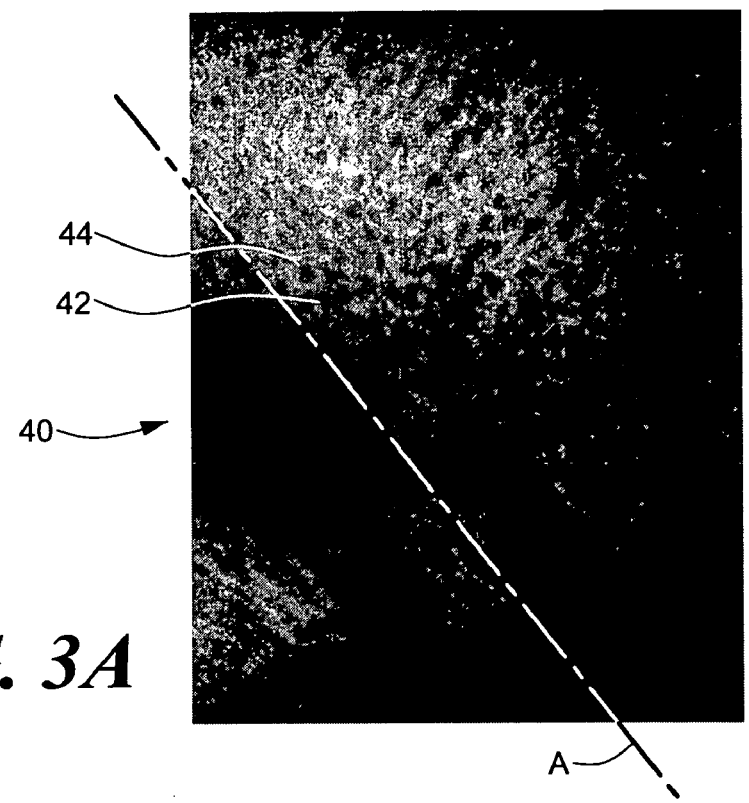
FIG. 3A is a first image obtained using a confocal microscope (in-vivo), which represents a tumor and/or lesion having a plurality of cells exhibiting elongated nuclei that are commonly oriented along a longitudinal axis indicating the presence of cancer cells.

FIG. 3A, in conjunction with FIG. 1, shows a relatively high resolution (e.g., 30× power) confocal microscope image 40 taken in-vivo of a first test point 12a of the tumor 12 located on the forehead region 14 of the patient 16. The first confocal microscope image 40 (hereinafter referred to as "first tumor image 40") of the first test point 12a represents a portion of the tumor prior to excision of a first Mohs layer and prior to the treatment of the tumor with the contrast agent of the present invention. The first tumor image 40 of the first test point 12a of the tumor 12 shows a plurality of cell anomalies, such as biopsy-proven basal cell carcinoma (BCC). The BCC cells exhibit elongated nuclei having a polarization that is substantially in alignment with the axis "A." The plurality of oval shape nuclei 42 appear dark in color (low contrast), while the scant cytoplasm 44 appear relatively bright.

Figure 3B:
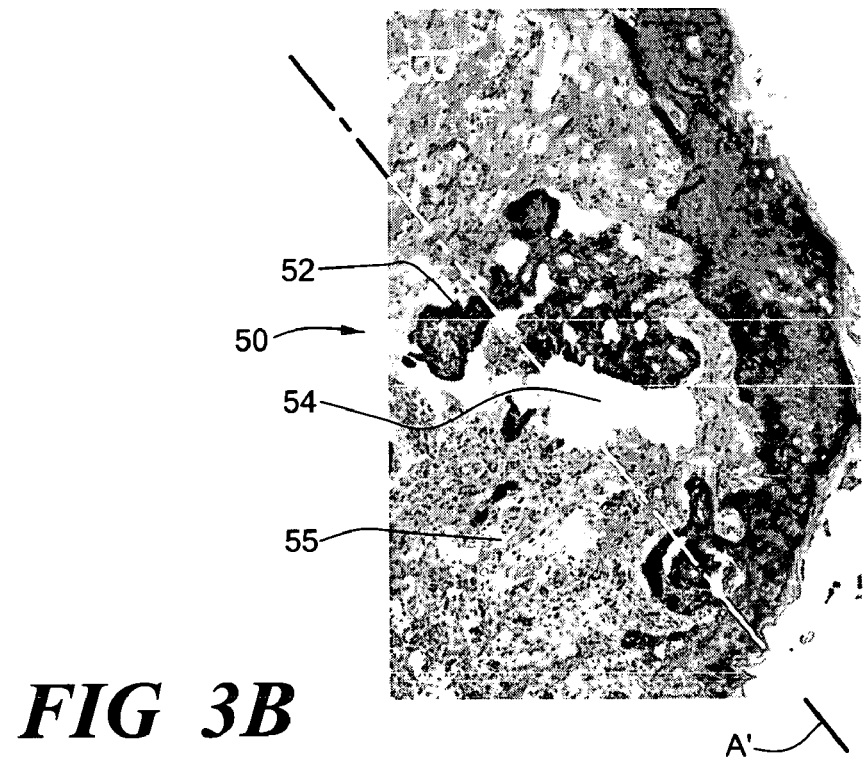
FIG. 3B is a second image obtained using a microscope (ex-vivo), which represent a first Mohs layer of the tumor and/or lesion of FIG. 3A and shows the plurality of cells having relatively dark nuclei surrounded by relatively lighter cytoplasm that verifies the presence of cancer cells.

FIG. 3B, in conjunction with FIG. 1, shows a relatively low resolution (e.g., 20× power) microscope image 50 taken ex-vivo of the first test point 12a of the tumor 12 located on the forehead region 14 of the patient 16. More specifically, the microscope image 50 (hereinafter referred to as "second tumor image 50") of the first test point 12a of the tumor 12 represents the tumor after excision of the first Mohs layer and prior to the treatment of the tumor 12 with the contrast agent of the present invention, which is described in detail below. The second tumor image 50 of the first test point verifies that the initially viewed elongated cell anomalies of the first tumor image (FIG. 3A), as defined by the parallel cellular orientations with respect to the longitudinal axis A', is BCC. In FIG. 3B, the BCC is shown as having relatively dark nuclei 52 surrounded by relatively lighter cytoplasm 54, which is separated from the surrounding stroma 55.

Figure 4B:
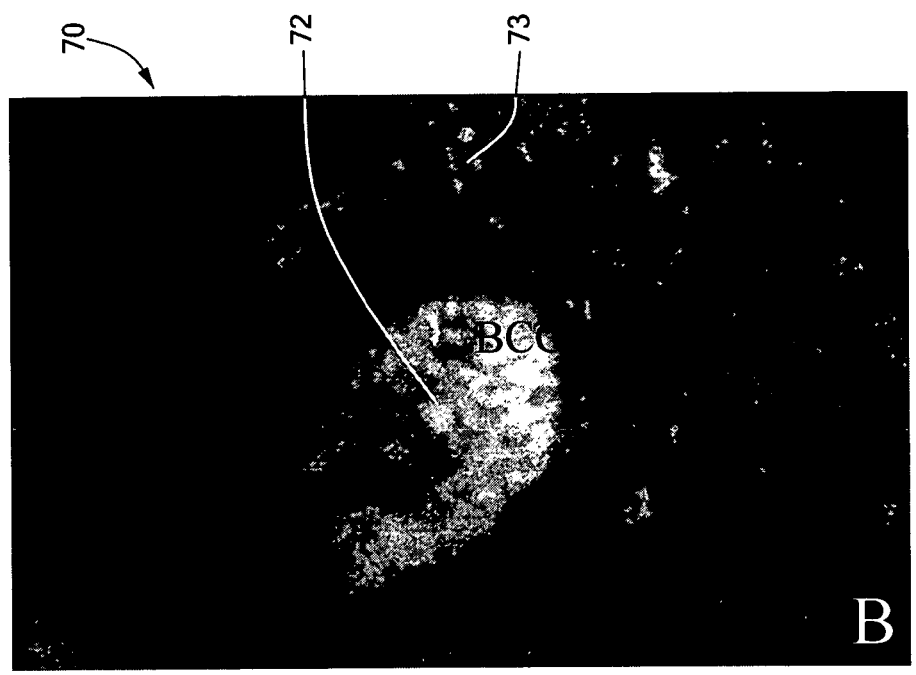
FIG. 4B is an enhanced third image obtained using the confocal microscope (in-vivo), which represents the Mohs defect area located on the tumor and/or lesion after treatment with a predetermined contrasting solution for enhancing the contrast and/or brightness of the formerly dark centrally oriented plurality of cells of FIG. 4A.
Figure 4A:
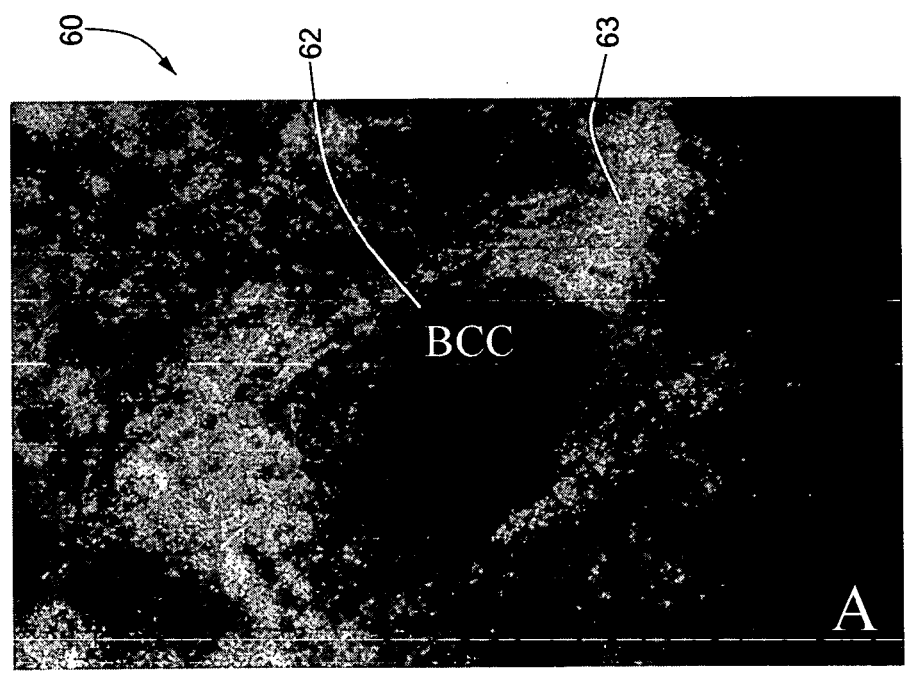
FIG. 4A is a third image obtained using the confocal microscope (in-vivo), which represents a Mohs defect area located on the tumor and/or lesion and depicts a dark plurality of cells representing the presence of cancer cells.

FIG. 4A, in conjunction with FIG. 1, shows another relatively high resolution (e.g., 30× power) confocal microscope image 60 of the first test point 12a taken in-vivo of the Mohs defect area 12d, which is defined as the remaining wound area located on the forehead region 14 of the patient 16 after excision of the first Mohs layer of the tumor 12, as described above. The confocal microscope image 60 (hereinafter referred to as "third tumor image 60") of the first test point of the Mohs defect area represents the tumor 12 prior to the treatment of the tumor with the contrast agent of the present invention. The third tumor image of the first test point 12a of the tumor 12 shows the centrally located BCC cells 62 as having relatively dark nuclei that can be difficult to identify and delineate from the surrounding stroma 63.

Referring now to FIG. 4B, in conjunction with FIG. 1, shown is an enhanced confocal microscope image 70 (hereinafter referred to as "enhanced third tumor image 70") having improved contrast in accordance with principles of the present invention. More particularly, the enhanced third tumor image 70 represents the first test point 12a of the Mohs defect area 12d, as similarly described above with respect to FIG. 4A, however, the Mohs defect area 12d has been treated with the predetermined contrasting solution of the present invention. The centrally located BCC cells 72 of the enhanced third tumor image 70 are depicted as having relatively bright nuclei that can be relatively easy to identify and delineate from the surrounding stroma 73.

In an exemplary embodiment, the predetermined contrasting solution includes a solution having at least a predetermined percentage of Aluminum and at least a predetermined percentage of Chloride to form an Aluminum-Chloride (AlCl) solution. In one embodiment, the AlCl solution includes a concentration of approximately 20% to approximately 40% mixed with water or alcohol. In another embodiment, the AlCl solution includes a solution of AlCl (hexahydrate) 20% w/v in anhydrous ethyl alcohol (S.D. alcohol 40) 93% v/v.

In yet another embodiment, the predetermined contrasting solution can include an acetic acid solution. In one embodiment, the acetic acid solution includes a concentration of approximately 5% to approximately 10% mixed with water or alcohol. The acetic acid solution can be used on excised Mohs layers (not shown) to enhance the contrast of nuclei relative to the surrounding cytoplasm and dermis. The BCC nuclei of the excised Mohs layer will appear intensely bright, similar to BCC nuclei of FIG. 4B after the application of the AlCl solution. However, one advantage of using AlCl over acetic acid as the predetermined contrasting solution is that the former can be applied in-vivo on intact skin or on open superficial wounds where it serves as a hemostatic agent, as well as an excellent exogenous contrast enhancer. On the other hand, acetic acid while acting as an excellent ex-vivo contrast enhancer, should not be used in-vivo because it may cause chemical burns of the skin structures. More particularly, acetic acid may cause compaction of chromatin within nuclei due to extraction of histone proteins.

Figure 5A:
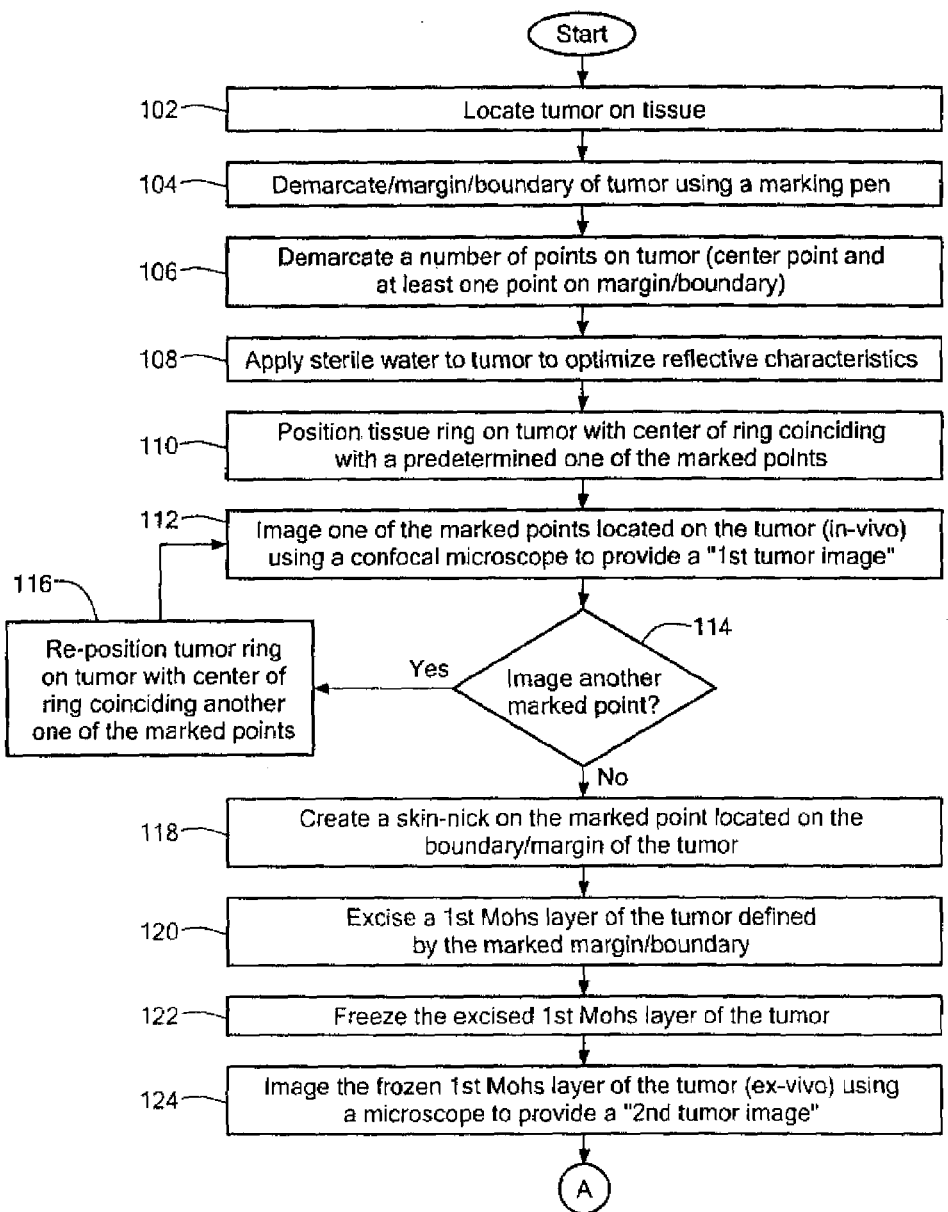
FIGS. 5A and 5B depict a flow chart illustrating a method executable on the system of FIG. 1 for imaging tumors.
Figure 5B:
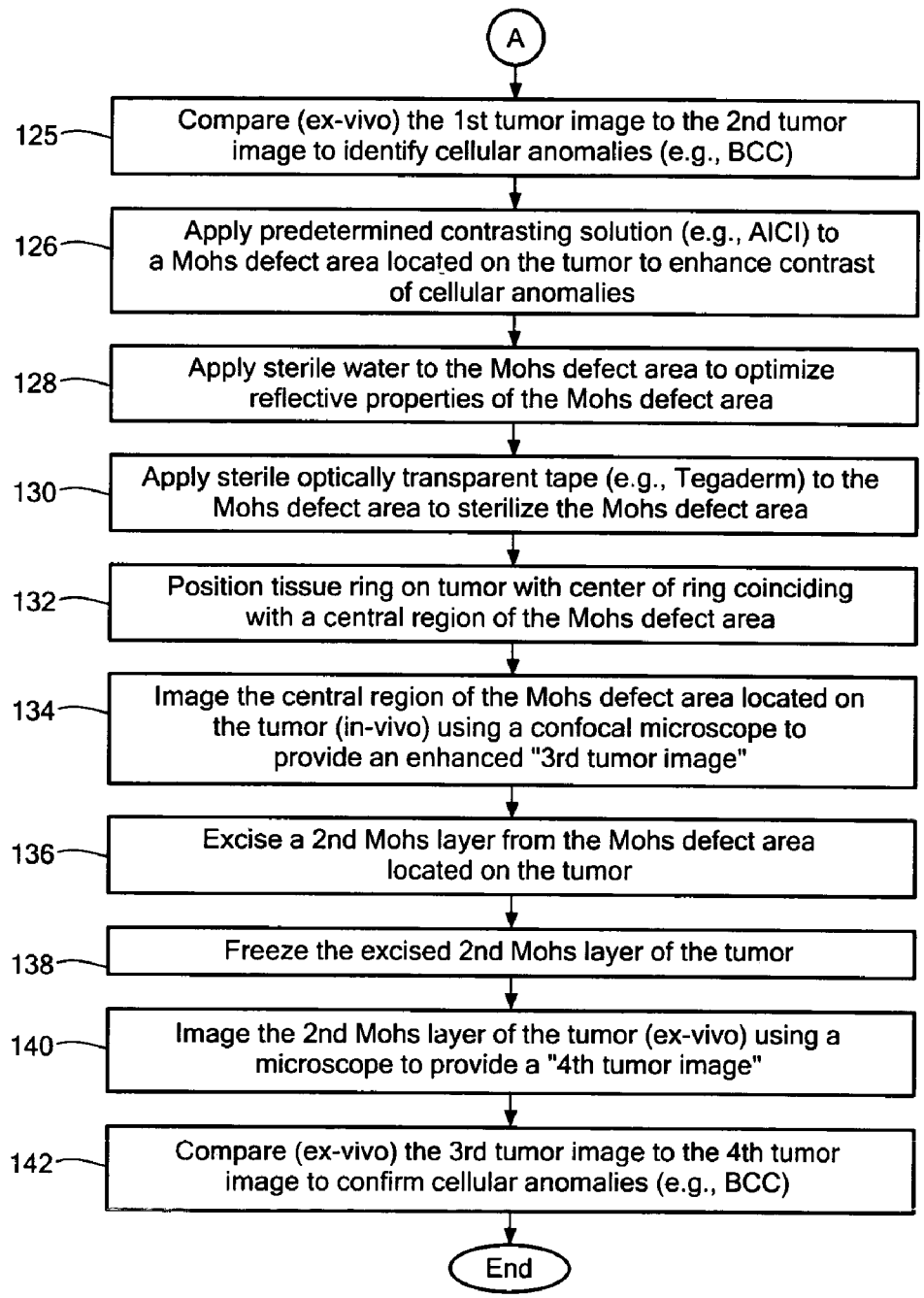

FIGS. 5A and 5B, in conjunction with FIGS. 1 and 2, depict a method 100 executable on the system 10 of FIG. 1 for imaging tumors, such as the tumor 12 located on the forehead region 14 of the patient 16. The method 100 provides one or more images of the tumor 12 that exhibit improved contrast, so that a surgeon can demarcate and remove the tumor 12, while at the same time, the method 100 minimizes the unnecessary removal of healthy normal tissue surrounding the tumor 12.

At step 102, the method 100 commences by visually locating the tumor 12 on the forehead region 14 of the patient 16. At step 104, a boundary 12b of the tumor 12 is marked using a surgical marking pen (not shown), such as a Sharpee marking pen. At step 106, a number of points on the tumor 12 can also be marked using the surgical marking pen. In the exemplary embodiment, the number of points marked on the tumor 12 of the patient 16 includes marking a first point on a central region of the tumor 12, which serves as the first test point 12a for imaging the tumor 12. Further, at least a second point 12c is marked on and crosses the previously marked boundary of the tumor and onto healthy skin or tissue of the forehead region 14 of the patient 16. The second mark 12c serves as a second image point, as well as a registration point that indicates the radial position of the tumor 12 to a surgeon after excision of the tumor 12.

At step 108, sterile water is applied to the tumor 12 to optimize reflective properties of the tumor 12. At step 110, the tissue ring 30 is positioned on the tumor 12 with the center of the tissue ring 30 substantially coinciding with the first test point 12a, which is centrally located on the tumor 12. At step 112, the imaging system 18 is controlled to be lowered downwardly along the negative z-axis (FIG. 1) to seat the objective lens 18a of the imaging system 18 into the tissue ring 30. The imaging system 18 is further controlled to take at least a first confocal image of the first test point 12a of the tumor 12, which is located of the forehead region 14 of the patient 16. In the exemplary embodiment, the first confocal image is represented by the first tumor image 40 shown and described above with respect to FIG. 3A.

At step 114, it is decided whether to confocal image another one of the number of marked points located on the tumor 12, such as the second point 12c. If it is determined at step 114 to obtain one or more confocal images of the second point 12c of the tumor 12, at step 116, the tissue ring 30 is re-positioned on the tumor 12 with the center of the tissue ring 30 substantially coinciding with the second test point, and the above method 100 is again directed to step 112 for repeating the process of obtaining one or more confocal images of the second test point. It should be understood that the number of marked points defined on the tumor 12, as described above in connection with step 106, can define a plurality of test points for subsequent confocal imaging should it be desired to inspect cellular structures and/or orientations at other locations of the tumor 12.

At step 114, if it is determined not to image another test point of the tumor 12, the method 100 further includes creating a skin-nick (not shown) using a scalpel or other surgical instrument on the second point 12c of the tumor 12. The skin nick formed on the second point 12c of the tumor 12 provides a registration point on the excised Mohs layer, which assists a surgeon in orienting the excised Mohs layer. At step 120, a first Mohs layer of the tumor 12 is excised along the marked boundary, which boundary is defined above with respect to step 104. Although not specifically shown, it should be recognized that this first Mohs layer typically includes a relatively thin sheet of skin including from the out-most layer of the skin to the inner most layer of the skin, the stratum corneum layer, the epidermis and at least a first portion of the dermis layer.

At step 122, the excised first Mohs layer of the tumor 12 is frozen by immersing the first Mohs layer in a predetermined freezing solution, such as liquid nitrogen or an OCT embedding solution and/or compound. At step 124, the excised and frozen first Mohs layer of the tumor 12 is imaged using a relatively low power microscope to provide a second tumor image, which in the exemplary embodiment is represented by the second tumor image 50 shown and described above with respect to FIG. 3B. At step 125, the first tumor image 40 (FIG. 3A) is compared to the second tumor image 50 (FIG. 3B) for verifying the presence of cellular anomalies, such as BCC.

At step 126, a predetermined contrasting solution is applied on a Mohs defect area 12d located on the forehead region 14 of the patient 16, which is defined by the wound formed by the excision of the first Mohs layer. In the exemplary embodiment, the predetermined contrasting solution includes Aluminum-Chloride (AlCl), having a predetermined ratio of Al to Cl. It should be understood that although AlCl is provided as an exemplary contrasting solution, a number of variations of this solution can also be provided as a contrasting solution in accordance with aspects of the present invention.

At step 128, sterile water is applied to the Mohs defect area 12*d* for optimizing the reflective characteristics of the Mohs defect area 12*d*. At step 130, an optically transparent sterile tape (not shown), such as Tegaderm tape, is applied to the Mohs defect area 12*d* for sterilizing the Mohs defect area 12*d* and for stabilizing any excessive bleeding at the Mohs defect area 12*d*. At step 132, the tissue ring 30 is positioned on the Mohs defect area 12*d* with the center of the tissue ring 30 substantially coinciding with the location of the first test point 12*a*. At step 134, the imaging system 18 is controlled to be lowered downwardly along the negative z-axis to seat the objective lens 18*a* thereof into the tissue ring 30 and at least one enhanced confocal image of the central point of the Mohs defect area 12*d* is obtained. In the exemplary embodiment, the enhanced confocal image of the central point of the Mohs defect area 12*d* is represented by the enhanced third tumor image shown and described above with respect to FIG. 4B.

In FIG. 4B, the presence of cellular anomalies, such as BCC, is evidenced by the centrally located BCC cells 72, which exhibit a relatively bright nuclei. The enhanced contrast of the BCC cells 72 is particularly helpful in providing a visual aid to a surgeon during surgical removal of the cellular anomalies and also aids the surgeon in minimizing the unnecessary removal of healthy tissue, which surrounds the BCC cells 72.

Referring again to FIG. 5B, in conjunction with FIGS. 1 and 2, at step 136, a second Mohs layer (not shown) of the tumor 12 is excised along the marked boundary in a similar manner as described above with respect to step 120. Although not specifically shown, it should be understood that the second Mohs layer typically includes a relatively thin sheet of skin including at least a second portion of the dermis layer. At step 138, the excised second Mohs layer of the tumor 12 is frozen by immersing the second Mohs layer in the predetermined freezing solution, as similarly described above with respect to step 122. At step 140, the frozen second Mohs layer is imaged using a microscope to provide a fourth tumor image (not shown). Although the fourth tumor image is not specifically shown, the fourth tumor image may be similar to the second tumor image (FIG. 3B), if cellular anomalies (e.g., BCC) are still present. At step 142, the enhanced third tumor image, which corresponds to the enhanced third tumor image of FIG. 4B, is compared to the fourth tumor image to confirm whether cellular anomalies are still present. It should be understood that the above described method 100 may be cyclically repeated for removing successive layers of tissue until it is determined that cellular anomalies (e.g., BCC) are no longer present.

Having thus described at least one illustrative embodiment of the invention, various alterations, modifications and improvements will readily occur to those skilled in the art. Such alterations, modifications and improvements are intended to be within the scope and spirit of the invention. Accordingly, the foregoing description is by way of example only and is not intended as limiting. The invention's limit is defined only in the following claims and the equivalents thereto. All references and publications cited herein are expressly incorporated herein by reference in their entirety.

What is claimed is:

1. A method of enhancing optical characteristics of at least one cell anomaly associated with a tumor, comprising:
    (a) applying a predetermined contrasting solution comprising an AlCl solution to an in-vivo defect area associated with the tumor for optically enhancing the at least one cell anomaly associated with the tumor; and
    (b) imaging at least a portion of the in-vivo defect area associated with the tumor using a first optical imaging system to provide an in-vivo enhanced tumor image, wherein the in-vivo enhanced tumor image includes the at least one cell anomaly having enhanced attributes.

2. The method of claim 1 wherein applying the predetermined contrasting solution comprising an AlCl solution to the in-vivo defect area comprises applying the AlCl solution having a predetermined concentration of Al and a predetermined concentration of Cl.

3. The method of claim 1 wherein applying the predetermined contrasting solution comprising an AlCl solution to the in-vivo defect area comprises applying a solution of AlCl (hexahydrate) 20% w/v in anhydrous ethyl alcohol (S.D. alcohol 40) 93% v/v.

4. The method of claim 2 wherein applying the AlCl solution having a predetermined concentration of Al and a predetermined concentration of Cl comprises applying an AlCl solution having a concentration ranging from approximately 20% to approximately 40%.

5. The method of claim 2, further comprising:
    (c) freezing an excised predetermined layer of the in-vivo defect area associated with the tumor.

6. The method of claim 5, further comprising:
    (d) imaging the excised predetermined layer of the in-vivo defect area associated with the tumor using a second predetermined optical imaging system to provide an ex-vivo enhanced tumor image.

7. The method of claim 6, further comprising:
    (e) comparing the in-vivo enhanced tumor image and the ex-vivo tumor image to investigate the presence of the at least one cell anomaly.

8. The method of claim 1 wherein after step (a), the method further comprises:
    applying sterile water to the in-vivo defect area for further optically enhancing the at least one cell anomaly.

9. The method of claim 8 wherein after step (a), the method further comprises:
    applying an optically transparent sterile tape to the in-vivo defect area for sterilizing the in-vivo defect area.

10. The method of claim 1 wherein imaging using the first optical imaging system comprises imaging using a confocal microscope.

11. The method of claim 6 wherein imaging using the second predetermined optical imaging system comprises imaging using a microscope.

* * * * *

UNITED STATES PATENT AND TRADEMARK OFFICE
CERTIFICATE OF CORRECTION

| | |
|---|---|
| PATENT NO. | : 7,128,894 B1 |
| APPLICATION NO. | : 10/607630 |
| DATED | : October 31, 2006 |
| INVENTOR(S) | : Tannous et al. |

It is certified that error appears in the above-identified patent and that said Letters Patent is hereby corrected as shown below:

Column 1, line 7, delete "claims benefit" and replace with -- claims the benefit --.

Column 3, line 2, delete ", which represent" and replace with -- , which represents --.

Column 6, line 18, delete "located of the" and replace with -- located at the --.

Signed and Sealed this

Twenty-second Day of May, 2007

JON W. DUDAS
*Director of the United States Patent and Trademark Office*